US012409118B2

(12) United States Patent
Nakatani et al.

(10) Patent No.: US 12,409,118 B2
(45) Date of Patent: Sep. 9, 2025

(54) EXTERNAL SKIN PREPARATION

(71) Applicant: KAO CORPORATION, Tokyo (JP)

(72) Inventors: Arisu Nakatani, Sumida-ku (JP); Nobuo Takazawa, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 143 days.

(21) Appl. No.: 17/759,666

(22) PCT Filed: Jan. 29, 2021

(86) PCT No.: PCT/JP2021/003138
§ 371 (c)(1),
(2) Date: Jul. 28, 2022

(87) PCT Pub. No.: WO2021/153705
PCT Pub. Date: Aug. 5, 2021

(65) Prior Publication Data
US 2023/0118811 A1    Apr. 20, 2023

(30) Foreign Application Priority Data
Jan. 31, 2020   (JP) .................................. 2020-015777

(51) Int. Cl.
| | | |
|---|---|---|
| *A61K 8/34* | (2006.01) | |
| *A61K 8/04* | (2006.01) | |
| *A61K 8/25* | (2006.01) | |
| *A61K 8/37* | (2006.01) | |
| *A61K 8/41* | (2006.01) | |
| *A61K 8/49* | (2006.01) | |
| *A61K 8/73* | (2006.01) | |
| *A61K 8/891* | (2006.01) | |
| *A61K 8/898* | (2006.01) | |
| *A61Q 17/04* | (2006.01) | |

(52) U.S. Cl.
CPC .............. *A61K 8/347* (2013.01); *A61K 8/046* (2013.01); *A61K 8/25* (2013.01); *A61K 8/37* (2013.01); *A61K 8/415* (2013.01); *A61K 8/4966* (2013.01); *A61K 8/738* (2013.01); *A61K 8/891* (2013.01); *A61K 8/898* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 4,710,371 A | 12/1987 | Palinczar | |
| 6,165,450 A * | 12/2000 | Chaudhuri | A61K 8/27 424/59 |
| 6,170,706 B1 * | 1/2001 | Havlovitz | B05B 9/0877 222/530 |
| 6,759,052 B1 | 7/2004 | Suzuki et al. | |

FOREIGN PATENT DOCUMENTS

| | | | |
|---|---|---|---|
| CN | 110520100 A | 11/2019 | |
| JP | 62-265215 A | 11/1987 | |
| JP | 3-247699 | 11/1991 | |
| JP | 4-221306 A | 8/1992 | |
| JP | 2000-281552 A | 10/2000 | |
| JP | 2003-63927 A | 3/2003 | |
| JP | 2004-244333 A | 9/2004 | |
| JP | WO 2011/049247 A1 | 4/2011 | |
| JP | 2011148722 A * | 8/2011 | |
| JP | 2014-19688 A | 2/2014 | |
| JP | 2016-6029 A | 1/2016 | |
| JP | 2017-71602 A | 4/2017 | |
| JP | WO 2019/044327 A1 | 3/2019 | |
| JP | 2019-135218 A | 8/2019 | |
| JP | WO 2019/176555 A1 | 9/2019 | |
| JP | 2020-94004 A | 6/2020 | |
| KR | 20020009938 A * | 2/2002 | |
| KR | 20080085301 A * | 9/2008 | |
| TW | 201625203 A | 7/2016 | |

OTHER PUBLICATIONS

Machine Translation of JP-2011148722-A (Year: 2011).*
Machine Translation of JP20020009938 (Year: 2002).*
Machine Translation of KR20080085301 (Year: 2008).*
Notice of Reasons for Refusal issued on Nov. 14, 2023, in corresponding Japanese Patent Application No. 2021-012595 (with machine translation).
Decision to grant a patent issued on Apr. 16, 2024, in corresponding Japanese Patent Application No. 2021-012595 (with machine translation).
International Search Report issued Apr. 13, 2021 in PCT/JP2021/003138, filed on Jan. 29, 2021, 2 pages.
Margaux Reese "What are iron oxides & why are they used in skincare" Iron Oxides in Skincare: Benefits, Uses, & More, Nov. 4, 2024, 9 pages total https://www.colorescience.com/blogs/blog/what-are-iron-oxides#4.
Authors et. al.: Disclosed Anonymously "Tinosorb S Lite Aqua brings Tinosorb S (Bis-Ethylhexyloxyphenol Methoxyphenyl Triazine, BEMT) into the water phase", IP.COM Inc, No. IPCOM000251025D, Sep. 29, 2017, 251 pages.
"Gelling Agents" INNOSPEC, Jan. 1, 2025, 3 pages total.
Authors et al.: Disclosed Anonymously "Suncare compositions with new cosmetic raw materials (3)" IP.COM.INC, No. IPCOM000203068D, Jan. 18, 2011, 169 pages total.

(Continued)

*Primary Examiner* — Jennifer A Berrios
(74) *Attorney, Agent, or Firm* — Oblon, McClelland, Maier & Neustadt, L.L.P.

(57) ABSTRACT

An external skin preparation is described, and contains an oil-soluble ultraviolet absorber, 0.5% by mass or more and 20% by mass or less of an oil gelling agent, and 50% by mass or more of a non-aqueous volatile component. The external skin preparation is unlikely to drip upon application, provides an impression from use of less oiliness and less tightness, is likely to have a uniform distribution of the oil-soluble ultraviolet absorber on the skin surface after application to the skin, and has an excellent ultraviolet protection effect.

20 Claims, 1 Drawing Sheet

(56) References Cited

OTHER PUBLICATIONS

Authors et al.: Disclosed Anonymously "Stable cosmetic preparation and ultraviolet absorber solution for cosmetic preparation" IP.COM.INC, No. IPCOM000204140D, Feb. 14, 2011, 120 pages total.

Disclosed Anonymously "Suncare compositions with new cosmetic raw materials (7)" IP.COM.INC, No. IPCOM000244537D, Dec. 18, 2015, 171 pages total.

* cited by examiner

Example 7          Comparative Example 1
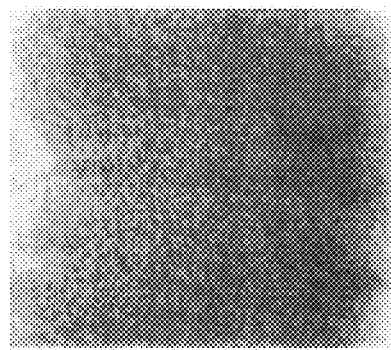 

EXTERNAL SKIN PREPARATION

CROSS-REFERENCE TO RELATED APPLICATIONS

The present application is a 35 U.S.C. § 371 national stage application of International patent application PCT/JP2021/003138, filed Jan. 29, 2021, which is based on and claims the benefit of priority to Japanese Application No. 2020-015777, filed Jan. 31, 2020. The entire contents of these applications are incorporated herein by reference.

FIELD OF THE INVENTION

The present invention relates to an external skin preparation.

BACKGROUND OF THE INVENTION

To obtain an ultraviolet protection effect, many external skin preparations in which an ultraviolet absorber is blended have conventionally been developed. As such an external skin preparation, for example, a specific skin cosmetic containing an ultraviolet absorber, a polymer having a hydrophilic segment including N-acylalkyleneimine as a repeating unit and an organopolysiloxane segment as constitutional units, an alcohol having from 1 to 4 carbon atoms, a powder having a number average particle size of from 1 to 10 μm, a powder having a number average particle size of more than 10 μm and 25 μm or less, and a propellant is known, which is considered as being excellent in durability of the ultraviolet protection effect (Patent Literature 1).

(Patent Literature 1) JP-A-2016-6029

SUMMARY OF THE INVENTION

The present invention provides an external skin preparation comprising the following components (A), (B), and (C):
(A) an oil-soluble ultraviolet absorber;
(B) 0.5% by mass or more and 20% by mass or less of an oil gelling agent; and
(C) 50% by mass or more of a non-aqueous volatile component.

DETAILED DESCRIPTION OF THE INVENTION

The present inventors conducted studies and found that, after the skin cosmetic described in Patent Literature 1 is applied to the skin, the cosmetic falls into the wrinkle and fine texture of the skin on the skin surface and the ultraviolet absorber is likely to be distributed in a non-uniform manner, which may result in an insufficient ultraviolet protection effect.

In addition, the external skin preparation using an oil-soluble ultraviolet absorber is required to have less oiliness (oily feeling) and less tightness and is also required to be unlikely to drip on the skin surface.

The present invention relates to providing an external skin preparation which is unlikely to drip upon application, provides an impression from use of less oiliness and less tightness, is likely to have a uniform distribution of the oil-soluble ultraviolet absorber on the skin surface after application to the skin, and has an excellent ultraviolet protection effect.

The present inventors found that an external skin preparation in which not only an oil-soluble ultraviolet absorber, but also a specific amount of an oil gelling agent and a high content of a non-aqueous volatile component are combined is unlikely to drip upon application, provides an impression from use of less oiliness and less tightness, is likely to have a uniform distribution of the oil-soluble ultraviolet absorber on the skin surface after application to the skin, and has an excellent ultraviolet protection effect, thereby completing the present invention.

The external skin preparation of the present invention is unlikely to drip upon application, provides an impression from use of less oiliness and less tightness, is likely to have a uniform distribution of the oil-soluble ultraviolet absorber on the skin surface after application to the skin, and has an excellent ultraviolet protection effect.

BRIEF DESCRIPTION OF DRAWINGS

FIG. 1 is images of application films of stock liquids of Example 7 and Comparative Example 1 photographed by VISIA-CR (manufactured by Canfield Scientific).

COMPONENT (A)

The external skin preparation of the present invention contains (A) an oil-soluble ultraviolet absorber.

As used herein, the oil-soluble ultraviolet absorber means an ultraviolet absorber having a solubility in water of less than 0.01% by mass.

Examples of the oil-soluble ultraviolet absorber include a benzoic acid-based oil-soluble ultraviolet absorber, an anthranilic acid-based oil-soluble ultraviolet absorber, an salicylic acid-based oil-soluble ultraviolet absorber, a cinnamic acid-based oil-soluble ultraviolet absorber, a benzoylmethane-based oil-soluble ultraviolet absorber, a triazine-based oil-soluble ultraviolet absorber, a benzophenone-based oil-soluble ultraviolet absorber, and a hydantoin-based oil-soluble ultraviolet absorber. Among them, one or more selected from the group consisting of a benzoic acid-based oil-soluble ultraviolet absorber, a cinnamic acid-based oil-soluble ultraviolet absorber, and a triazine-based oil-soluble ultraviolet absorber are preferable.

Examples of the benzoic acid-based oil-soluble ultraviolet absorber include p-aminobenzoic acid, glyceryl p-aminobenzoic acid, ethyl dihydroxypropyl p-aminobenzoic acid, octyl dimethyl p-aminobenzoic acid, amyl p-dimethylamino benzoate, and diethylamino hydroxybenzoyl hexyl benzoate.

Examples of the anthranilic acid-based oil-soluble ultraviolet absorber include methyl anthranilate.

Examples of the salicylic acid-based oil-soluble ultraviolet absorber include homomenthyl salicylate, 2-ethylhexyl salicylate, and triethanolamine salicylate.

Examples of the cinnamic acid-based oil-soluble ultraviolet absorber include 2-ethylhexyl p-methoxycinnamate, glyceryl mono-2-ethylhexanoate di-p-methoxy cinnamate, methyl 2,5-diisopropylcinnamate, methylbis(trimethylsiloxy)silylisopentyl trimethoxycinnamate, isopropyl p-methoxycinnamate, isopropyl p-methoxycinnamate-diisopropylcinnamate esters mixture, 2-ethoxyethyl p-methoxycinnamate, and p-methoxycinnamic acid diethanol amine salt.

Examples of the benzoylmethane-based oil-soluble ultraviolet absorber include 4-isopropyldibenzoylmethane and 4-tert-butyl-4'-methoxydibenzoylmethane.

Examples of the triazine-based oil-soluble ultraviolet absorber include 2,4,6-tris[4-(2-ethylhexyloxycarbonyl)anilino]-1,3,5-triazine and 2,4-bis-[{4-(2-ethylhexyloxy)-2-hydroxy}-phenyl]-6-(4-methoxyphenyl)-1,3,5-triazine.

Examples of the benzophenone-based oil-soluble ultraviolet absorber include 2,4-dihydroxybenzophenone, 2,2'-dihydroxy-4-methoxybenzophenone, 2-hydroxy-4-methoxybenzophenone, 2,2'-dihydroxy-4,4'-dimethoxybenzophenone, 2,2'4,4'-tetrahydroxybenzophenone, 4-(2-β-glucopyranosiloxy)propoxy-2-hydroxybenzophenone and 2-hydroxy-4-n-octyloxybenzophenone.

Examples of the hydantoin-based oil-soluble ultraviolet absorber include 2-ethylhexyl dimethoxybenzylidene dioxo-imidazolidine propionate.

Examples of other oil-soluble ultraviolet absorbers include octocrylene, cinoxate, phenylbenzimidazole sulfonic acid, 1-(3,4-dimethoxyphenyl)-4,4-dimethyl-1,3-pentanedione, 3-(4-methylbenzyliden)camphor, and methylene bis-benzotriazolyl tetramethylbutylphenol.

The oil-soluble ultraviolet absorber can be roughly classified into oil-soluble ultraviolet absorbers in a solid state at 1 atmosphere at 25° C. and oil-soluble ultraviolet absorbers in a liquid state at 1 atmosphere at 25° C. In the present invention, it is preferable to use at least an oil-soluble ultraviolet absorber in a liquid state at 1 atmosphere at 25° C. as the oil-soluble ultraviolet absorber. In this case, the oil-soluble ultraviolet absorber in a solid state at 1 atmosphere at 25° C. may be used in combination with an oil-soluble ultraviolet absorber in a liquid state at 1 atmosphere at 25° C.

For example, diethylamino hydroxybenzoyl hexyl benzoate, 2,4,6-tris[4-(2-ethylhexyloxycarbonyl)anilino]-1,3,5-triazine, and 2,4-bis-[{4-(2-ethylhexyloxy)-2-hydroxy}-phenyl]-6-(4-methoxyphenyl)-1,3,5-triazine exemplified above are oil-soluble ultraviolet absorbers in a solid state at 1 atmosphere at 25° C. Moreover, 2-ethylhexyl p-methoxycinnamate, isopropyl p-methoxycinnamate, 2-ethoxyethyl p-methoxycinnamate, and the like exemplified above are oil-soluble ultraviolet absorbers in a liquid state at 1 atmosphere at 25° C.

The oil-soluble ultraviolet absorber may be used alone or in combination of two or more thereof.

A content of the oil-soluble ultraviolet absorber is preferably 5% by mass or more, more preferably 7.5% by mass or more, further more preferably 10% by mass or more, and particularly preferably 12.5% by mass or more based on the external skin preparation of the present invention from the viewpoint of ultraviolet protection effect, application uniformity, and the like, and preferably 30% by mass or less, more preferably 25% by mass or less, further more preferably 20% by mass or less, and particularly preferably 17.5% by mass or less based on the external skin preparation of the present invention from the viewpoint of application uniformity, absence of strong oiliness and strong tightness, and the like. The specific range is preferably 5% by mass or more and 30% by mass or less, more preferably 7.5% by mass or more and 25% by mass or less, further more preferably 10% by mass or more and 20° by mass or less, and particularly preferably 12.5% by mass or more and 17.5° by mass or less based on the external skin preparation of the present invention. When the content of the oil-soluble ultraviolet absorber is 7.5% by mass or more, the application uniformity and ultraviolet protection effect are particularly improved, and when a content of the oil-soluble ultraviolet absorber is 25% by mass or less, the application uniformity is improved in particular.

When the external skin preparation of the present invention is an aerosol type external skin preparation, the above content of the oil-soluble ultraviolet absorber means the ratio when a stock liquid is taken as 100% by mass. Hereinafter, the same applies to other components.

Component (B)

The external skin preparation of the present invention contains (B) an oil gelling agent.

Examples of the oil gelling agent include one or more selected from the group consisting of a sugar fatty acid ester-based oil gelling agent, a glycerin fatty acid ester-based oil gelling agent, an amino acid derivative-based oil gelling agent, and a benzylidene sorbitol-based oil gelling agents. Among them, a sugar fatty acid ester-based oil gelling agent, a glycerin fatty acid ester-based oil gelling agent, and an amino acid derivative-based oil gelling agent are preferable, and a sugar fatty acid ester-based oil gelling agent is more preferable from the viewpoint of application uniformity, ultraviolet protection effect, being unlikely to drip upon application, absence of strong oiliness and strong tightness, and the like.

The residues of the fatty acids of sugar fatty acid ester-based oil gelling agents and glycerin fatty acid ester-based oil gelling agents are preferably linear or branched saturated fatty acid residues. The number of carbon atoms of the fatty acid residue is preferably from 8 to 24, more preferably from 12 to 22, and particularly preferably from 14 to 20.

Examples of the sugar fatty acid ester-based oil gelling agent include dextrin fatty acid ester-based oil gelling agents such as dextrin myristate, dextrin palmitate, dextrin stearate, dextrin palmitate/2-ethylhexanoate, and dextrin palmitate/hexyldecanoate; sucrose fatty acid ester-based oil gelling agents such as sucrose palmitate and sucrose stearate; inulin fatty acid ester-based oil gelling agents such as inulin stearate; and fructooligosaccharide fatty acid ester-based oil gelling agents such as fructooligosaccharide stearate and fructooligosaccharide 2-ethylhexanoate.

Examples of the glycerin fatty acid ester-based oil gelling agent include glyceryl behenate/eicosadioate, glyceryl tribehenate/isostearate/eicosandioate, and polyglyceryl-10 behenate/eicosadioate.

Examples of the amino acid derivative-based oil gelling agent include dibutyl lauroyl glutamide and dibutyl ethylhexanoyl glutamide.

Examples of the benzylidene sorbitol-based oil gelling agent include monobenzylidenesorbitol and dibenzylidenesorbitol.

Among the oil gelling agents as described above, a dextrin fatty acid ester-based oil gelling agent is preferable, and dextrin palmitate is particularly preferable from the viewpoint of application uniformity, ultraviolet protection effect, being unlikely to drip upon application, absence of strong oiliness and strong tightness, and the like.

The oil gelling agent to be used may be a commercial product or may be obtained through synthesis in accordance with a conventional method. Examples of commercial products of dextrin myristate include Rheopearl MKL2 (manufactured by Chiba Flour Milling Co., Ltd.). Examples of commercial products of dextrin palmitate include Rheopearl KL2 and Rheopearl TL2 (all manufactured by Chiba Flour Milling Co., Ltd.). Examples of commercial products of dextrin palmitate/2-ethylhexanoate include Rheopearl TT2 (manufactured by Chiba Flour Milling Co., Ltd.). Examples of commercial products of dextrin palmitate/hexyldecanoate include Rheopearl WX (manufactured by Chiba Flour Milling Co., Ltd.). Examples of commercial products of inulin stearate include Rheopearl ISL2 and Rheopearl ISK2 (all manufactured by Chiba Flour Milling Co., Ltd.). Examples of commercial products of dibutyl ethylhexanoyl glutamide include amino acid gelling agent EB-21 (manufactured by AJINOMOTO CO., INC.).

The oil gelling agent may be used alone or in combination of two or more thereof.

A content of the oil gelling agent is 0.5% by mass or more and 20% by mass or less based on the external skin preparation of the present invention. When the content of the oil gelling agent is 0.5° by mass or more, dripping is unlikely to occur upon application, the application uniformity of the components on the skin after application is improved, and an excellent ultraviolet protection effect can be obtained. In addition, when the content of the oil gelling agent is 20% by mass or less, the oiliness and tightness are reduced.

The content of the oil gelling agent is preferably 1% by mass or more, more preferably 1.5% by mass or more, further more preferably 2% by mass or more, and particularly preferably 2.5% by mass or more based on the external skin preparation of the present invention from the viewpoint of application uniformity, ultraviolet protection effect, being unlikely to drip upon application, and the like, and is preferably 15% by mass or less, more preferably 10% by mass or less, further more preferably 7.5% by mass or less, and particularly preferably 5% by mass or less based on the external skin preparation of the present invention from the viewpoint of absence of strong oiliness and strong tightness and ease of production. The specific range is preferably 1% by mass or more and 15% by mass or less, more preferably 1.5% by mass or more and 10% by mass or less, further more preferably 2% by mass or more and 7.5% by mass or less, and particularly preferably 2.5% by mass or more and 5% by mass or less based on the external skin preparation of the present invention.

A mass ratio of the component (B) to the component (A), [(B)/(A)], is preferably 0.01 or more, more preferably 0.05 or more, further more preferably 0.1 or more, and particularly preferably 0.15 or more from the viewpoint of application uniformity, ultraviolet protection effect, being unlikely to drip upon application, and the like, and is preferably 1.5 or less, more preferably 1 or less, further more preferably 0.6 or less, and particularly preferably 0.3 or less from the viewpoint of application uniformity, ultraviolet protection effect, absence of strong oiliness and strong tightness, and the like. The specific range is preferably 0.01 or more and 1.5 or less, more preferably 0.05 or more and 1 or less, further more preferably 0.1 or more and 0.6 or less, and particularly preferably 0.15 or more and 0.3 or less.

Component (C)

The external skin preparation of the present invention contains (C) a non-aqueous volatile component.

The non-aqueous volatile component means any volatile component other than water. As used herein, the "volatile component" refers to a component which exhibit volatility at 1 atmosphere at 25° C., and the "non-volatile component" refers to a component which is non-volatile at 1 atmosphere at 25° C.

Examples of the non-aqueous volatile component include one or more selected from the group consisting of (C-1) a volatile silicone oil, (C-2) a lower alcohol, and (C-3) a volatile liquid oil other than the volatile silicone oil. The external skin preparation of the present invention is preferably those containing at least a component (C-1) as the component (C) or those containing at least a component (C-2) as the component (C), and more preferably those containing the components (C-1) and (C-2), from the viewpoint of impression from use (absence of strong oiliness and strong tightness), application uniformity of the components on the skin after application, discharge properties in the case of using the external skin preparation as a spray, and the like. When the component (C-1) is contained, the impression from use (absence of strong oiliness and strong tightness) can be improved. When the component (C-2) is contained, the impression from use (absence of strong oiliness and strong tightness) and discharge properties in the case of using the external skin preparation as a spray are improved. In particular, when the component (C-2) is contained, good discharge properties and quick drying properties can be obtained even in the case of using the external skin preparation as a spray having a high content of the oil gelling agent.

(Component (C-1))

Any volatile silicone oil may be used so long as it is in a liquid state at 1 atmosphere at 25° C., and examples thereof include decamethylcyclopentasiloxane, octamethylcyclotetrasiloxane, dodecamethylcyclohexasiloxane, methyl trimethicone, decamethyltetrasiloxane, octamethyl trisiloxane, ethyl trisiloxane, and volatile dimethylpolysiloxane. These may be used alone or in combination of two or more thereof. The kinematic viscosity of volatile dimethylpolysiloxane at 25° C. is preferably 0.5 $mm^2/s$ or more and 2 $mm^2/s$ or less, and more preferably 0.65 $mm^2/s$ or more and 2 $mm^2/s$ or less.

Examples of commercial products of decamethylcyclopentasiloxane include TFS405 (manufactured by Momentive Performance Materials Japan LLC.), SH245 and DC345 (manufactured by Dow Corning Toray Co., Ltd.), and KF-995 (manufactured by Shin-Etsu Chemical Co., Ltd.). Examples of commercial products of methyl trimethicone include silicone TMF-1.5 (manufactured by Shin-Etsu Chemical Co., Ltd.). Examples of commercial products of decamethyltetrasiloxane include KF-96L-1.5CS (manufactured by Shin-Etsu Chemical Co., Ltd.). Examples of commercial products of ethyl trisiloxane include SILSOFTETS (manufactured by Momentive Performance Materials Japan LLC.). Examples of commercial products of dimethylpolysiloxane include KF-96L-2CS (manufactured by Shin-Etsu Chemical Co., Ltd.).

(Component (C-2))

The lower alcohol is preferably a linear or branched monohydric alcohol having from 1 to 6 carbon atoms, and more preferably a linear or branched saturated monohydric alcohol having from 1 to 6 carbon atoms. The number of carbon atoms of the lower alcohol is preferably from 1 to 4, and more preferably from 2 to 3.

Examples of the lower alcohol include ethanol, n-propanol, isopropanol, and butanol, and these may be used alone or in combination of two or more thereof. Among them, ethanol or isopropanol is preferable, and ethanol is more preferable, from the viewpoint of discharge properties in the case of using the external skin preparation as a spray.

(Component (C-3))

Examples of the volatile liquid oil other than the volatile silicone oil include a volatile hydrocarbon oil.

Any volatile hydrocarbon oil may be used so long as it has a flash point of 35° C. or more and 100° C. or less and is in a liquid state at 1 atmosphere at 25° C., and examples thereof include paraffin volatile hydrocarbon oils such as n-decane, n-undecane, and n-dodecane; and isoparaffin volatile hydrocarbon oils such as isodecane, isododecane, and light isoparaffin. These may be used alone or in combination of two or more thereof.

The non-aqueous volatile component may be used alone or in combination of two or more thereof.

A content of the non-aqueous volatile component is 50% by mass or more based on the external skin preparation of the present invention. When the content of the non-aqueous volatile component is 50° by mass or more, dripping is unlikely to occur upon application.

The content of the non-aqueous volatile component is preferably 52% by mass or more, more preferably 55% by mass or more, further more preferably 60% by mass or more, and particularly preferably 62% by mass or more based on the external skin preparation of the present invention from the viewpoint of application uniformity, ultraviolet protection effect, formulation stability, and the like, and is preferably 90% by mass or less, more preferably 85% by mass or less, further more preferably 80% by mass or less, and particularly preferably 75% by mass or less based on the external skin preparation of the present invention from the viewpoint of ultraviolet protection effect and the like. The specific range is preferably 52% by mass or more and 90° by mass or less, more preferably 55% by mass or more and 85° by mass or less, further more preferably 60% by mass or more and 80° by mass or less, and particularly preferably 62% by mass or more and 75% by mass or less based on the external skin preparation of the present invention.

When a volatile silicone oil is used as the component (C), a content of the volatile silicone oil is preferably 0.5% by mass or more, more preferably 1% by mass or more, further more preferably 2% by mass or more, and particularly preferably 4% by mass or more based on the external skin preparation of the present invention from the viewpoint of ultraviolet protection effect, application uniformity, impression from use (suppression of the stickiness and oiliness derived from the non-volatile oil), and the like, and is preferably 30% by mass or less, more preferably 25% by mass or less, further more preferably 20% by mass or less, particularly preferably 15% by mass or less based on the external skin preparation of the present invention from the viewpoint of clarity, compatibility with non-volatile oils, application uniformity, ultraviolet protection effect, formulation stability, and the like. The specific range is preferably 0.5% by mass or more and 30% by mass or less, more preferably 1% by mass or more and 25% by mass or less, further more preferably 2% by mass or more and 20% by mass or less, and particularly preferably 4% by mass or more and 15° by mass or less based on the external skin preparation of the present invention.

When a lower alcohol is used as the component (C), a content of the lower alcohol is preferably 40% by mass or more, more preferably 45% by mass or more, and further more preferably 50% by mass or more based on the external skin preparation of the present invention from the viewpoint of absence of strong oiliness and strong tightness, discharge properties in the case of using the external skin preparation as a spray, and the like, and is preferably 95% by mass or less, more preferably 90% by mass or less, and further more preferably 80% by mass or less based on the external skin preparation of the present invention from the viewpoint of ultraviolet protection effect, formulation stability, and the like. The specific range is preferably 40% by mass or more and 95% by mass or less, more preferably 45% by mass or more and 90% by mass or less, and further more preferably 50% by mass or more and 80% by mass or less based on the external skin preparation of the present invention.

A mass ratio of the component (A) to the component (C), [(A)/(C)], is preferably 0.01 or more, more preferably 0.05 or more, further more preferably 0.1 or more, and particularly preferably 0.15 or more from the viewpoint of ultraviolet protection effect, application uniformity, and the like, and is preferably 1.5 or less, more preferably 1 or less, and further more preferably 0.5 or less from the viewpoint of application uniformity, and the like. The specific range is preferably 0.01 or more and 1.5 or less, more preferably 0.05 or more and 1 or less, further more preferably 0.1 or more and 0.5 or less, and particularly preferably 0.15 or more and 0.5 or less.

A mass ratio of the components (A) and (B) in total to the component (C), [((A)+(B))/(C)], is preferably 0.02 or more, more preferably 0.05 or more, further more preferably 0.1 or more, and particularly preferably 0.23 or more from the viewpoint of application uniformity, absence of strong oiliness and strong tightness, being unlikely to drip upon application, ultraviolet protection effect, and the like, and is preferably 3 or less, more preferably 0.8 or less, further more preferably 0.6 or less, and particularly preferably 0.3 or less from the same viewpoint as above. The specific range is preferably 0.02 or more and 3 or less, more preferably 0.05 or more and 0.8 or less, further more preferably 0.1 or more and 0.6 or less, and particularly preferably 0.23 or more and 0.3 or less.

A mass ratio of the component (C-2) to the component (C-1), [(C-2)/(C-1)], is preferably 0.5 or more, more preferably 1 or more, further more preferably 3 or more, and particularly preferably 6 or more, and is preferably 600 or less, more preferably 100 or less, further more preferably 25 or less, and particularly preferably 9 or less from the viewpoint of ultraviolet protection effect, application uniformity, and the like. The specific range is preferably 0.5 or more and 600 or less, more preferably 1 or more and 100 or less, further more preferably 3 or more and 25 or less, and particularly preferably 6 or more and 9 or less.

The external skin preparation of the present invention preferably further contains one or more selected from the group consisting of (D) a non-volatile liquid oil (provided that the component (A) is excluded) and (E) a film forming agent, in addition to the components (A) to (C), more preferably contains the components (A) to (D), and particularly preferably contains the components (A) to (E). When the component (D) is further contained in addition to the components (A) to (C), formulation stability, application uniformity, and the like are improved. When the component (E) is further contained in addition to the components (A) to (C), ultraviolet protection effect, application uniformity, water resistance, friction resistance, and the like are improved.

Component (D)

Any non-volatile liquid oil may be used so long as it is other than the component (A) and in a liquid state at 1 atmosphere at 25° C., and examples thereof include not only non-volatile ester oils, but also non-volatile hydrocarbon oils such as liquid isoparaffin, heavy liquid isoparaffin, and squalane; and non-volatile silicone oils such as non-volatile dimethylpolysiloxane and non-volatile methylphenylpolysiloxane. Among them, a non-volatile ester oil is preferable from the viewpoint of compatibility, application uniformity, ultraviolet protection effect, and the like.

Examples of the non-volatile ester oil include non-volatile fatty acid ester oils and non-volatile aromatic carboxylic acid ester oils. Examples of the non-volatile aromatic carboxylic acid ester oil include C12-15 alkyl benzoate.

The residue of the fatty acid of the non-volatile fatty acid ester oil is preferably a linear or branched fatty acid residue.

The number of carbon atoms of the fatty acid residue is preferably from 8 to 24, more preferably from 12 to 22, and particularly preferably from 14 to 20 from the viewpoint of compatibility, application uniformity, ultraviolet protection effect, and the like.

Examples of the non-volatile fatty acid ester oil include non-volatile monohydric alcohol fatty acid ester oils and non-volatile polyhydric alcohol fatty acid ester oils. Among them, a non-volatile monohydric alcohol fatty acid ester oil is preferable from the viewpoint of compatibility, application uniformity, ultraviolet protection effect, and the like. The non-volatile monohydric alcohol fatty acid ester oil is a non-volatile ester oil of fatty acid and a monohydric alcohol. The residue of the monohydric alcohol in the ester oil is preferably the residue of a linear or branched monohydric alcohol having from 3 to 20 carbon atoms, more preferably the residue of a linear or branched monohydric alcohol having from 3 to 14 carbon atoms, and particularly preferably the residue of a linear or branched monohydric alcohol having from 3 to 8 carbon atoms from the viewpoint of compatibility, application uniformity, ultraviolet protection effect and the like.

Examples of the non-volatile monohydric alcohol fatty acid ester oil include cetyl 2-ethylhexanoate, isononyl isononanoate, isotridecyl isononanoate, isopropyl myristate, isopropyl palmitate, 2-ethylhexyl palmitate, 2-ethylhexyl stearate, and stearyl stearate.

Examples of the non-volatile polyhydric alcohol fatty acid ester oil include fatty acid triglycerides such as caprylic/capric triglyceride and glyceryl tri(2-ethylhexanoate); and an ester oil of fatty acid and neopentyl glycol such as neopentyl glycol dicaprate and neopentyl glycol diethylhexanoate.

Examples of commercial products of liquid isoparaffin include ParLeam 6 (manufactured by NOF CORPORATION). Examples of commercial products of non-volatile dimethylpolysiloxane include KF-96A-10CS (manufactured by Shin-Etsu Chemical Co., Ltd.). Examples of commercial products of isopropyl palmitate include EXCEPARL IPP (manufactured by Kao Corporation). Examples of commercial products of C12-15 alkyl benzoate include FINSOLV TN (manufactured by Innospec Active Chemicals). Examples of commercial products of neopentyl glycol dicaprate include ESTEMOL N-01 (manufactured by the Nisshin OilliO Group, Ltd.).

In the present invention, it is preferable to use not only the volatile silicone oil as the component (C) but also the above non-volatile ester oil, from the viewpoint of achieving excellent impression from use, excellent application uniformity, and excellent ultraviolet protection effect at the same time, since the volatile silicone oil becomes more compatible with the oil-soluble ultraviolet absorber without separation.

The non-volatile liquid oil of the component (D) may be used alone or in combination of two or more thereof.

A content of the non-volatile liquid oil of the component (D) is preferably 0.1% by mass or more, more preferably 0.5% by mass or more, and further more preferably 1% by mass or more based on the external skin preparation of the present invention from the viewpoint of compatibility, application uniformity, ultraviolet protection effect, storage stability, and the like, and is preferably 35% by mass or less, more preferably 25% by mass or less, further more preferably 20% by mass or less, and particularly preferably 10% by mass or less based on the external skin preparation of the present invention from the viewpoint of application uniformity, ultraviolet protection effect, and the like. The specific range is preferably 0.1° by mass or more and 35% by mass or less, more preferably 0.5% by mass or more and 25% by mass or less, further more preferably 1% by mass or more and 20% by mass or less, and particularly preferably 1% by mass or more and 10% by mass or less based on the external skin preparation of the present invention.

A mass ratio of the component (B) to the components (A) and (D) in total, [(B)/((A)+(D))], is preferably 0.01 or more, more preferably 0.05 or more, and further more preferably 0.1 or more from the viewpoint of application uniformity, ultraviolet protection effect, and the like, and is preferably 1 or less, more preferably 0.5 or less, further more preferably 0.25 or less, and particularly preferably 0.18 or less from the same viewpoint as above. The specific range is preferably 0.01 or more and 1 or less, more preferably 0.05 or more and 0.5 or less, further more preferably 0.1 or more and 0.25 or less, and particularly preferably 0.1 or more and 0.18 or less.

Component (E)

Examples of the film forming agent include silicone-based film forming agents and (meth)acrylic film forming agents, but from the viewpoint of ultraviolet protection effect, water resistance, friction resistance, and the like, silicone-based film forming agents are preferable. In addition, the film forming agent is preferably oil soluble.

As used herein, the silicone-based film forming agent refers to a film forming agent having a silicone segment in its molecule, and the position of the silicone segment in the molecule is arbitrary, and may be, for example, positioned in the main chain or the side chain of the polymer. The silicone segment may have a linear structure or a branched structure. Examples of the silicone segment having a branched structure include a dendrimer type siloxane segment, a silsesquioxane segment, and a silicone segment having a network molecular structure.

Examples of the silicone-based film forming agent include poly(N-acylalkyleneimine) modified silicones such as oxazoline modified silicone; amino modified silicones such as amodimethicone, aminoethylaminopropyl dimethicone, and aminopropyl dimethicone; fluorine modified silicones; trimethylsiloxysilicate; trimethylsiloxysilicate/dimethiconol crosspolymer; (meth)acrylic polymers having a dendrimer type siloxane structure in a side chain, such as acrylates/polytrimethylsiloxymethacrylate copolymer; polyalkylsilsesquioxanes such as polymethylsilsesquioxane and polypropylsilsesquioxane; and (meth)acrylic silicone-based graft copolymers such as acrylates/dimethicone copolymer, acrylates/ethylhexyl acrylate/dimethicone methacrylate copolymer, acrylates/stearyl acrylate/dimethicone methacrylate copolymer, and acrylates/behenyl acrylate/dimethicone methacrylate copolymer. These may be used alone or in combination of two or more thereof.

Among them, a poly(N-acylalkyleneimine) modified silicone and trimethylsiloxysilicate are preferable, and a poly(N-acylalkyleneimine) modified silicone, or a combination of a poly(N-acylalkyleneimine) modified silicone and trimethylsiloxysilicate are more preferable from the viewpoint of water resistance, ease of production, and the like.

(Poly(N-Acylalkyleneimine) Modified Silicone)

The above poly(N-acylalkyleneimine) modified silicone is preferably an organopolysiloxane (hereinafter, this organopolysiloxane also refers to an organopolysiloxane (OX)) in which poly(N-acylalkyleneimine) segments are bonded to at least two silicon atoms of an organopolysiloxane segment forming the main chain via cationic divalent linking groups, the poly(N-acylalkyleneimine) segments consisting of repeating units of the following formula (1):

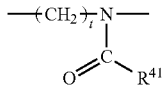
(1)

wherein $R^{41}$ represents a hydrogen atom, an alkyl group having from 1 to 22 carbon atoms, an aralkyl group, or an aryl group, and t represents 2 or 3, wherein the number average molecular weight of the poly(N-acylalkyleneimine) segment is from 500 to 4000, and the weight average molecular weight of the organopolysiloxane segment forming the main chain is from 10000 to 200000.

Here, the organopolysiloxane (OX) will be described in detail.

At least two poly(N-acylalkyleneimine) segments are bonded to an arbitrary silicon atom constituting the organopolysiloxane segment via cationic divalent linking groups, but are preferably bonded to one or more silicon atoms excluding the silicon atoms at both ends of the organopolysiloxane segment via cationic divalent linking groups, and are more preferably bonded to two or more silicon atoms excluding the silicon atoms at both ends via cationic divalent linking groups.

The cationic divalent linking group serves as a linking group of the poly(N-acylalkyleneimine) segment.

Examples of the cationic divalent linking group include alkylene groups containing a cationic group. The cationic divalent linking group is preferably an alkylene group having from 2 to 20 carbon atoms and containing from 1 to 3 cationic groups, and more preferably an alkylene group having from 2 to 20 carbon atoms and containing from 1 to 3 cationic groups which are one or more selected from the group consisting of a primary amino group, a secondary amino group, a tertiary amino group, and a quaternary ammonium group.

Among such cationic divalent linking groups, any one group of the following formulas (A1) to (A9) is preferable, any one group of the formulas (A1) to (A4) is more preferable, and any one group of the formula (A1) or (A2) is particularly preferable.

In the formula, An⁻ represents a counterion of a quaternary ammonium salt. Examples thereof include halide ions (such as a chloride ion and an iodide ion), sulfate ions, phosphate ions, acetate ions, lactate ions, p-toluenesulfonate ions, perchlorate ions, and monoalkyl nitrate ions (such as methyl sulfate ion and ethyl sulfate ion).

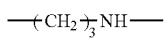
(A1)

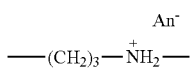
(A2)

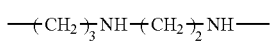
(A3)

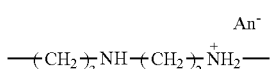
(A4)

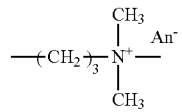
(A5)

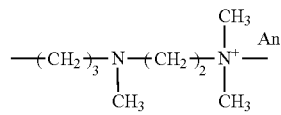
(A6)

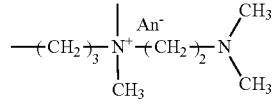
(A7)

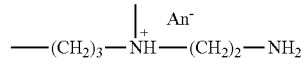
(A8)

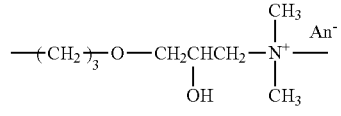
(A9)

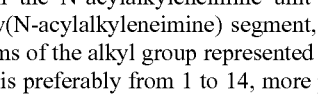

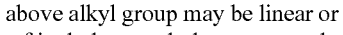

In the N-acylalkyleneimine unit which constitutes the poly(N-acylalkyleneimine) segment, the number of carbon atoms of the alkyl group represented by $R_{41}$ is from 1 to 22, but is preferably from 1 to 14, more preferably from 1 to 6, and particularly preferably from 1 to 3, in the formula (1). The above alkyl group may be linear or branched. Examples thereof include a methyl group, an ethyl group, an n-propyl group, an isopropyl group, an n-butyl group, a tert-butyl group, a pentyl group, and a hexyl group.

As the aralkyl group represented by $R^{41}$, an aralkyl group having from 7 to 15 carbon atoms is preferable. Examples thereof include a benzyl group, a phenethyl group, a trityl group, a naphthylmethyl group, and an anthracenylmethyl group.

As the aryl group represented by $R^{41}$, an aryl group having from 6 to 14 carbon atoms is preferable. Examples thereof include a phenyl group, a tolyl group, a xylyl group, a naphthyl group, a biphenyl group, an anthracenyl group, and a phenanthryl group.

Among them, $R^{41}$ is preferably a hydrogen atom or a linear or branched alkyl group having from 1 to 3 carbon atoms, and more preferably a linear or branched alkyl group having from 1 to 3 carbon atoms.

In the formula (1), t represents 2 or 3, but is preferably 2.

A mass ratio of the organopolysiloxane segment (a) forming the main chain and the poly(N-acylalkyleneimine) segment (b), (a)/(b), is preferably from 40/60 to 98/2, more preferably from 45/55 to 82/18, further more preferably from 60/40 to 80/20, further more preferably from 65/35 to 80/20, further more preferably from 68/32 to 80/20, and particularly preferably from 70/30 to 79/21.

As used herein, the mass ratio (a)/(b) refers to a value obtained from an integration ratio of the alkyl group or the phenyl group in the organopolysiloxane segment to the methylene group in the poly(N-acylalkyleneimine) segment as measured by nuclear magnetic resonance ($^{1}$H-NMR) analysis using deuterated chloroform in which 5% by mass of the organopolysiloxane (OX) is dissolved.

In the organopolysiloxane (OX), the weight average molecular weight of the organopolysiloxane segment between adjacent poly(N-acylalkyleneimine) segments (hereinafter, also referred to as "MWg") is preferably from 1000 to 40000, more preferably from 1500 to 30000, and particularly preferably from 1750 to 5000.

As used herein, the "organopolysiloxane segment between adjacent poly(N-acylalkyleneimine) segments" refers to a segment surrounded by a dashed line as shown in the following formula (2) between two points, that is, a connection point of a poly(N-acylalkyleneimine) segment to the organopolysiloxane segment (connection point A) and a connection point of a poly(N-acylalkyleneimine) segment adjacent to the above poly(N-acylalkyleneimine) segment (connection point B), the segment being constituted by one $R^{42}SiO$ unit, one $R^{43}$, and y+1 $(R^{42})_2SiO$ units. Also, the "poly(N-acylalkyleneimine) segment" refers to the $-Z^{11}-R^{44}$ moiety bonded to the above $R^{43}$.

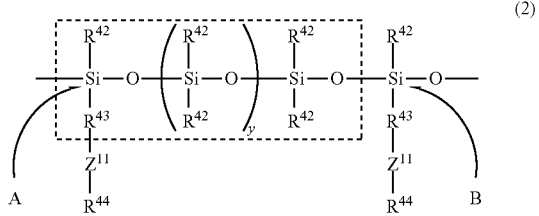

(2)

In the formula (2), each $R^{42}$ independently represents an alkyl group having from 1 to 22 carbon atoms or a phenyl group, $R^{43}$ represents a cationic divalent linking group, $-Z^{11}-R^{44}$ represents a poly(N-acylalkyleneimine) segment, $R^{44}$ represents a residue of a polymerization initiator or a hydrogen atom, and y represents a positive number. A plurality of $R^{42}$, $R^{43}$, and $R^{44}$ may be the same or different.

MWg represents the molecular weight of the segment surrounded by a dashed line in the above formula (2), which can be considered as the mass of the organopolysiloxane segment per 1 mol of the poly(N-acylalkyleneimine) segment (g/mol). When 100% of the functional groups of the modified organopolysiloxane serving as the raw material compound are substituted with poly(N-acylalkyleneimine), the substituted poly(N-acylalkyleneimine) equals to the functional group equivalent (g/mol) of the modified organopolysiloxane.

The molecular weight of the poly(N-acylalkyleneimine) segment can be calculated from the molecular weight and the degree of polymerization of the N-acylalkyleneimine unit, or measured by gel permeation chromatography (GPC), but as used herein, the molecular weight of the poly(N-acylalkyleneimine) segment refers to the number average molecular weight in terms of polystyrene (hereinafter, also referred to as MNox) as measured by GPC under the measurement conditions described below. MNox is preferably from 800 to 3500, and more preferably from 1000 to 3 000.

MWg can be obtained using a content (% by mass) of the organopolysiloxane segment forming the main chain (hereinafter, also referred to as Csi) by the following equation (I).

$$MWg = Csi \times MNox/(100-Csi) \qquad (I)$$

The weight average molecular weight of the organopolysiloxane segment forming the main chain (hereinafter, also referred to as MWsi) is preferably from 15000 to 160000, more preferably from 20000 to 150000, and particularly preferably from 25000 to 100000.

Since the organopolysiloxane segment forming the main chain has a common skeleton with the modified organopolysiloxane serving as the raw material compound, MWsi is substantially equal to the weight average molecular weight of the modified organopolysiloxane serving as the raw material compound. The weight average molecular weight of the modified organopolysiloxane serving as the raw material compound is the weight average molecular weight in terms of polystyrene measured by GPC under the following measurement conditions.

(Measurement Conditions for Weight Average Molecular Weight of Modified Organopolysiloxane)
Column: Super HZ4000+Super HZ2000 (manufactured by Tosoh Corporation)
Eluent: 1 mM triethylamine/THF
Flow rate: 0.35 mL/min
Column temperature: 40° C.
Detector: UV
Sample: 50 μL The weight average molecular weight of organopolysiloxane (OX) (hereinafter, also referred to as MWt) is preferably from 10000 to 500000, more preferably from 12000 to 200000, further more preferably from 25000 to 160000, and particularly preferably from 35000 to 150000. MWt refers to the value in terms of polystyrene as measured by GPC under the measurement conditions described below.

(Measurement Conditions for MNox and MWt)
Column: two K-804L (manufactured by Tosoh Corporation) are connected in series and used
Eluent: 1 mM dimethyldodecylamine/chloroform
Flow rate: 1.0 mL/min
Column temperature: 40° C.
Detector: RI
Sample: 50 μL When the poly(N-acylalkyleneimine) segment is a poly (N-propionylethyleneimine) segment, the $^1$H-NMR measurement for calculating the mass ratio (a)/(b) can be performed, for example, under the following conditions.

($^1$H-NMR Measurement Conditions)
A solution of 0.5 g of polymer sample in 2 g of measurement solvent (deuterated chloroform) is measured by $^1$H-NMR (400 MHz manufactured by Varian). Then, the ratio of silicone and poly(N-propionylethyleneimine) is calculated from each integrated value.
Pulse Sequence
Relax. delay: 30 seconds, —Pulse: 45 degrees, —Cumulative number: 8 times
Peak confirmed at around 0 ppm: methyl group in polydimethylsiloxane,
at around 3.4 ppm: methylene moiety in ethylene imine.

The organopolysiloxane (OX) may be obtained by synthesizing according to the methods described in JP-A-2008-143820, JP-A-2009-24114, JP-A-2015-67603, JP-A-2016-204336, and the like, and used. For example, the organopolysiloxane (OX) can be produced by reacting an organopolysiloxane modified with a functional group which induces the above cationic divalent linking group with a terminal reactive poly(N-acylalkyleneimine) which is obtained by carrying out ring-opening polymerization of a cyclic imino ether corresponding to the repeating unit of the formula (1).

Specific examples of the poly(N-acylalkyleneimine) modified silicone include a poly(N-formyl ethyleneimine) modified silicone, a poly(N-acetylethyleneimine) modified silicone, a poly(N-propionylethyleneimine) modified silicone, a poly(N-n-octanoylethyleneimine) modified silicone, a poly(N-n-dodecanoylethyleneimine) modified silicone, a poly(N-formylpropyleneimine) modified silicone, a poly(N- acetylpropyleneimine) modified silicone, a poly(N-propionylpropyleneimine) modified silicone, a poly(N-n-octanoylpropyleneimine) modified silicone, and a poly(N-n-dodecanoylpropyleneimine) modified silicone.

The film forming agent may be used alone or in combination of two or more thereof.

A content of the film forming agent is preferably 0.1% by mass or more, more preferably 0.5% by mass or more, further more preferably 0.75% by mass or more, and particularly preferably 1% by mass or more based on the external skin preparation of the present invention from the viewpoint of ultraviolet protection effect, water resistance, friction resistance, and the like, and is preferably 10% by mass or less, more preferably 7.5% by mass or less, further more preferably 5% by mass or less, and particularly preferably 4% by mass or less based on the external skin preparation of the present invention from the viewpoint of discharge properties in the case of using the external skin preparation as a spray, and the like (the term spray encompasses a mist formulation). The specific range is preferably 0.1° by mass or more and 10° by mass or less, more preferably 0.5° by mass or more and 7.5% by mass or less, further more preferably 0.75% by mass or more and 5% by mass or less, and particularly preferably 1% by mass or more and 4% by mass or less based on the external skin preparation of the present invention.

In addition to the above components, the external skin preparation of the present invention may contain an ultraviolet scattering agent, a powder other than the ultraviolet scattering agent (an organic powder, an inorganic powder, and an organic-inorganic composite powder), a surfactant, water, a water-soluble ultraviolet absorber, a fragrance, an animal or plant extract, a cooling agent, a preservative, an anti-inflammatory agent, an emollient, a pH regulator, a chelating agent, an antioxidant, a colorant, and the like. These may be used alone or in combination of two or more thereof.

A content of the ultraviolet scattering agent is preferably 0% by mass or more and 2.5% by mass or less, more preferably 0% by mass or more and 1% by mass or less, further more preferably 0% by mass or more and 0.5% by mass or less, and particularly preferably 0% by mass based on the external skin preparation of the present invention from the viewpoint of application uniformity, no white finish, impression from use (no friction feeling), and the like. With such a content of the ultraviolet scattering agent, the external skin preparation of the present invention can obtain an excellent ultraviolet protection effect.

A content of the surfactant is 0% by mass or more and 2.5% by mass or less, more preferably 0% by mass or more and 1% by mass or less, further more preferably 0% by mass or more and 0.5% by mass or less, and particularly preferably 0% by mass based on the external skin preparation of the present invention from the viewpoint of water resistance and the like.

A content of water is preferably 0% by mass or more and 10° by mass or less, more preferably 0° by mass or more and 5% by mass or less, further more preferably 0% by mass or more and 0.5% by mass or less, and particularly preferably 0% by mass based on the external skin preparation of the present invention from the viewpoint of water resistance, application uniformity of components on the skin after application, formulation stability, and the like.

The form of the external skin preparation of the present invention is not particularly limited, and may be, for example, a transparent liquid, an emulsion, a paste, a cream, a gel, a lotion, a spray (aerosol type or non-aerosol type), and a foam (aerosol type or non-aerosol type), or may be a sheet obtained by impregnating a base sheet with the external skin preparation of the present invention as the impregnation liquid. When the external skin preparation is an aerosol type external skin preparation, the container of the external skin preparation is usually a pressure proof container, and when the external skin preparation is in another form, examples of the container include a jar container, a bottle container, a squeezable container, a pump dispenser container, a pump mist container, and a trigger mist container. The external skin preparation of the present invention has good discharge properties even in the case of a spray containing an oil gelling agent, as described above.

Among the above, the form of the external skin preparation of the present invention is preferably a spray, more preferably an aerosol spray type external skin preparation or a non-aerosol spray type external skin preparation such as a pump mist type one and a trigger mist type one, and particularly preferably an aerosol spray type external skin preparation from the viewpoint of application uniformity, ultraviolet protection effect, impression from use, and the like.

Examples of the external skin preparation of the present invention (the stock liquid for an aerosol type external skin preparation) include an emulsion type external skin preparation (an oil-in-water type external skin preparation and a water-in-oil type external skin preparation), a multi-layer separation type external skin preparation, and an oil-based external skin preparation, but an oil-based external skin preparation is preferable from the viewpoint of achieving excellent water resistance, excellent application uniformity, and excellent ultraviolet protection effect at the same time.

As used herein, the oil-based external skin preparation refers to an external skin preparation in which an oil-soluble ultraviolet absorber and components other than the oil-soluble ultraviolet absorber in the external skin preparation are dissolved in each other. For example, one in which an oil-soluble ultraviolet absorber and components other than the oil-soluble ultraviolet absorber are dissolved in each other and which exhibits a transparent liquid state is encompassed in the oil-based external skin preparation, even when components other than the oil such as ethanol are contained.

The external skin preparation of the present invention (the stock liquid for the aerosol type external skin preparation) is preferably a liquid. The viscosity at 25° C. is preferably 0 mPa·s or more, and more preferably 2.5 mPa·s or more from the viewpoint of discharge properties and the like, and is preferably 20000 mPa·s or less, and more preferably 10000 mPa·s or less from the viewpoint of discharge properties and the like.

Then, when the external skin preparation of the present invention is an aerosol spray type external skin preparation, the viscosity of the stock liquid at 25° C. is preferably 0 mPa·s or more, more preferably 5 mPa·s or more, and further more preferably 10 mPa·s or more from the viewpoint of discharge properties and the like, and is preferably 10000 mPa·s or less, more preferably 2500 mPa·s or less, further more preferably 1500 mPa·s or less, and particularly preferably less than 500 mPa·s from the viewpoint of discharge properties and the like.

When the external skin preparation of the present invention is a non-aerosol spray type external skin preparation, the viscosity of the external skin preparation at 25° C. is, as described above, preferably 0 mPa·s or more, and more preferably 2.5 mPa·s or more from the viewpoint of discharge properties and the like, and is further more preferably 10 mPa·s or less, and particularly preferably 5 mPa·s or less from the viewpoint of discharge properties and the like.

When the external skin preparation of the present invention is an external skin preparation charged in a pump dispenser container, the viscosity of the external skin preparation at 25° C. is further more preferably 5000 mPa·s or more, and particularly preferably 5500 mPa·s or more from the viewpoint of discharge properties and the like, and is preferably 20000 mPa·s or less, and more preferably 15000 mPa·s or less from the same viewpoint.

When the external skin preparation of the present invention is an external skin preparation charged in a shaking-out container, such as a lotion, the viscosity of the external skin preparation at 25° C. is preferably 0 mPa·s or more, and more preferably 5 mPa·s or more from the viewpoint of impression from use and the like, and is preferably 10000 mPa·s or less, and more preferably 5000 mPa·s or less from the viewpoint of discharge properties, impression from use, and the like.

The above viscosity at 25° C. can be measured with a Brookfield Viscometer (B-type viscometer) and specifically, may be measured by the method described in Examples.

In the external skin preparation of the present invention (the stock liquid for an aerosol type external skin preparation), the viscosity at 25° C. after all volatile components (where water is not contained, (C) the non-aqueous volatile component) are volatilized is preferably 10000 mPa·s or more, more preferably 100000 mPa·s or more, further more preferably 200000 mPa·s or more, and particularly preferably 300000 mPa·s or more from the viewpoint of ultraviolet protection effect and the like. The upper limit value of the viscosity is not particularly limited, but may be, for example, 20000000 mPa·s.

The above viscosity at 25° C. after all the volatile components are volatilized may be measured by using a Brookfield Viscometer (B-type viscometer) after all the volatile components (where water is not contained, (C) the non-aqueous volatile component) are volatilized. It can also be measured by the method described in Examples.

Here, examples of the specific form of the aerosol type external skin preparation include the following aerosol type external skin preparation (α).

(α) An aerosol type external skin preparation in which a stock liquid containing the following components (A), (B), and (C):
(A) an oil-soluble ultraviolet absorber;
(B) 0.5% by mass or more and 20% by mass or less of an oil gelling agent based on the stock liquid; and
(C) 50% by mass or more of a non-aqueous volatile component based on the stock liquid,
(optionally, in addition, the component (D) and/or the component (E), and other components) and a propellant are charged in a pressure proof container, provided that the stock liquid is the total composition of the content of liquid excluding the propellant.

The aerosol type external skin preparation (a) may be an aerosol spray type or an aerosol foam type external skin preparation, and is preferably an aerosol spray type external skin preparation.

Examples of the propellant include liquefied petroleum gas (LPG), dimethyl ether (DME), carbon dioxide, nitrogen gas, and mixtures thereof. In addition, an alternative chlorofluorocarbon such as HFC-152a can be used.

A mass ratio of the stock liquid to the propellant (stock liquid/propellant) is preferably 10/90 or more, more preferably 20/80 or more, and particularly preferably 30/70 or more, and is preferably 99/1 or less, more preferably 85/15 or less, and particularly preferably 75/25 or less. The specific range is preferably 10/90 or more and 99/1 or less, more preferably 20/80 or more and 85/15 or less, and particularly preferably 30/70 or more and 75/25 or less. The amount of the propellant is preferably adjusted so as to be 0.12 MPa or more and 0.45 MPa or less at a temperature of 25° C.

The external skin preparation of the present invention is useful as a sunscreen. The external skin preparation of the present invention can be used as a sunscreen by applying to the skin (preferably the skin excluding the scalp, and more preferably the face, body, hand and foot, and the like) by a method in accordance with the type of the form.

The external skin preparation of the present invention can be produced in accordance with a conventional method. For an aerosol type external skin preparation, for example, the components (A), (B), and (C) (optionally, in addition, the component (D) and/or the component (E), and other components) may be mixed for dissolution or dispersion to prepare a stock liquid, and the resulting stock liquid may be charged into a pressure proof container with a propellant.

In relation to the aforementioned embodiments, the present invention further discloses the following external skin preparation and the like.

<1> An external skin preparation comprising the following components (A), (B), and (C):
(A) an oil-soluble ultraviolet absorber;
(B) 0.5% by mass or more and 20% by mass or less of an oil gelling agent; and
(C) 50% by mass or more of a non-aqueous volatile component.

<2> The external skin preparation according to <1>, wherein the component (A) is preferably one or more selected from the group consisting of a benzoic acid-based oil-soluble ultraviolet absorber, an anthranilic acid-based oil-soluble ultraviolet absorber, a salicylic acid-based oil-soluble ultraviolet absorber, a cinnamic acid-based oil-soluble ultraviolet absorber, a benzoylmethane-based oil-soluble ultraviolet absorber, a triazine-based oil-soluble ultraviolet absorber, a benzophenone-based oil-soluble ultraviolet absorber, and a hydantoin-based oil-soluble ultraviolet absorber, more preferably one or more selected from the group consisting of a benzoic acid-based oil-soluble ultraviolet absorber, a cinnamic acid-based oil-soluble ultraviolet absorber, and a triazine-based oil-soluble ultraviolet absorber, and further more preferably one or more selected from the group consisting of p-aminobenzoic acid, glyceryl p-aminobenzoic acid, ethyl dihydroxypropyl p-aminobenzoic acid, octyl dimethyl p-aminobenzoic acid, amyl p-dimethylamino benzoate, diethylamino hydroxybenzoyl hexyl benzoate, 2-ethylhexyl p-methoxycinnamate, glyceryl mono-2-ethylhexanoate di-p-methoxy cinnamate, methyl 2,5-diisopropylcinnamate, methylbis(trimethylsiloxy)silylisopentyl trimethoxycinnamate, isopropyl p-methoxycinnamate, isopropyl p-methoxycinnamate-diisopropylcinnamate esters mixture, 2-ethoxyethyl p-methoxycinnamate, p-methoxycinnamic acid diethanol amine salt, 2,4,6-tris[4-(2-ethylhexyloxycarbonyl)anilino]-1,3,5-triazine, and 2,4-bis-[{4-(2-ethylhexyloxy)-2-hydroxy}-phenyl]-6-(4-methoxyphenyl)-1,3,5-triazine.

<3> The external skin preparation according to <1>, preferably comprising at least an oil-soluble ultraviolet absorber in a liquid state at 1 atmosphere at 25° C. as the component (A).

<4> The external skin preparation according to any of <1> to <3>, wherein a content of the component (A) is preferably 5° by mass or more, more preferably 7.5° by mass or more, further more preferably 10° by mass or more, and particularly preferably 12.5% by mass or more based on the external skin preparation, and is preferably 30% by mass or less, more preferably 25% by mass or less, further more preferably 20% by mass or less, particularly preferably 17.5% by mass or less based on the external skin preparation.

<5> The external skin preparation according to any of <1> to <3>, wherein a content of the component (A) is preferably 5% by mass or more and 30% by mass or less, more preferably 7.5% by mass or more and 25% by mass or less, further more preferably 10% by mass or more and 20% by mass or less, and particularly preferably 12.5% by mass or more and 17.5° by mass or less based on the external skin preparation.

<6> The external skin preparation according to any of <1> to <5>, wherein the component (B) is preferably one or more selected from the group consisting of a sugar fatty acid ester-based oil gelling agent, a glycerin fatty acid ester-based oil gelling agent, an amino acid derivative-based oil gelling agent, and a benzylidene sorbitol-based oil gelling agent, more preferably one or more selected from the group consisting of a sugar fatty acid ester-based oil gelling agent, a glycerin fatty acid ester-based oil gelling agent, and an amino acid derivative-based oil gelling agent, and further more preferably a sugar fatty acid ester-based oil gelling agent.

<7> The external skin preparation according to <6>, wherein the sugar fatty acid ester-based oil gelling agent is preferably one or more selected from the group consisting of a dextrin fatty acid ester-based oil gelling agent, a sucrose fatty acid ester-based oil gelling agent, an inulin fatty acid ester-based oil gelling agent, and a fructooligosaccharide fatty acid ester-based oil gelling agent, more preferably one or more selected from the group consisting of dextrin myristate, dextrin palmitate, dextrin stearate, dextrin palmitate/2-ethylhexanoate, dextrin palmitate/hexyldecanoate, sucrose palmitate, sucrose stearate, inulin stearate, fructooligosaccharide stearate, and fructooligosaccharide 2-ethylhexanoate, and particularly preferably dextrin palmitate.

<8> The external skin preparation according to <6> or <7>, wherein the amino acid derivative-based oil gelling agent is one or more selected from the group consisting of dibutyl lauroyl glutamide and dibutyl ethylhexanoyl glutamide.

<9> The external skin preparation according to any of <1> to <8>, wherein a content of the component (B) is preferably 1% by mass or more, more preferably 1.5% by mass or more, further more preferably 2% by mass or more, and particularly preferably 2.5% by mass or more based on the external skin preparation, and is preferably 15% by mass or less, more preferably 10% by mass or less, further more preferably 7.5% by mass or less, and particularly preferably 5% by mass or less based on the external skin preparation.

<10> The external skin preparation according to any of <1> to <8>, wherein a content of the component (B) is preferably 1% by mass or more and 15% by mass or less, more preferably 1.5% by mass or more and 10% by mass or less, further more preferably 2% by mass or more and 7.5% by mass or less, and particularly preferably 2.5% by mass or more and 5% by mass or less based on the external skin preparation.

<11> The external skin preparation according to any of <1> to <10>, wherein a mass ratio of the component (B) to the component (A), [(B)/(A)], is preferably 0.01 or more, more preferably 0.05 or more, further more preferably 0.1 or more, and particularly preferably 0.15 or more, and is preferably 1.5 or less, more preferably 1 or less, further more preferably 0.6 or less, and particularly preferably 0.3 or less.

<12> The external skin preparation according to any of <1> to <10>, wherein a mass ratio of the component (B) to the component (A), [(B)/(A)], is preferably 0.01 or more and 1.5 or less, more preferably 0.05 or more and 1 or less, further more preferably 0.1 or more and 0.6 or less, and particularly preferably 0.15 or more and 0.3 or less.

<13> The external skin preparation according to any of <1> to <12>, wherein the component (C) is preferably one or more selected from the group consisting of (C-1) a volatile silicone oil, (C-2) a lower alcohol, and (C-3) a volatile liquid oil other than the volatile silicone oil.

<14> The external skin preparation according to any of <1> to <13>, preferably comprising at least (C-1) the volatile silicone oil as the component (C), and more preferably comprising (C-1) the volatile silicone oil and (C-2) the lower alcohol as the component (C).

<15> The external skin preparation according to any of <1> to <14>, wherein a content of the component (C) is preferably 52% by mass or more, more preferably 55% by mass or more, further more preferably 60% by mass or more, and particularly preferably 62% by mass or more based on the external skin preparation, and is preferably 90% by mass or less, more preferably 85% by mass or less, further more preferably 80% by mass or less, and particularly preferably 75% by mass or less based on the external skin preparation.

<16> The external skin preparation according to any of <1> to <14>, wherein a content of the component (C) is preferably 0.5° by mass or more and 30° by mass or less, more preferably 1% by mass or more and 25° by mass or less, further more preferably 2% by mass or more and 20% by mass or less, and particularly preferably 4% by mass or more and 15% by mass or less based on the external skin preparation.

<17> The external skin preparation according to any of <1> to <16>, wherein a content of (C-2) the lower alcohol is preferably 40% by mass or more, more preferably 45% by mass or more, and further more preferably 50% by mass or more based on the external skin preparation, and is preferably 95% by mass or less, more preferably 90% by mass or less, and further more preferably 80% by mass or less based on the external skin preparation.

<18> The external skin preparation according to any of <1> to <17>, wherein a mass ratio of the component (A) to the component (C), [(A)/(C)], is preferably 0.01 or more, more preferably 0.05 or more, further more preferably 0.1 or more, and particularly preferably 0.15 or more, and is preferably 1.5 or less, more preferably 1 or less, and further more preferably 0.5 or less.

<19> The external skin preparation according to any of <1> to <17>, wherein a mass ratio of the component (A) to the component (C), [(A)/(C)], is preferably 0.01 or more and 1.5 or less, more preferably 0.05 or more and 1 or less, further more preferably 0.1 or more and 0.5 or less, and particularly preferably 0.15 or more and 0.5 or less.

<20> The external skin preparation according to any of <1> to <19>, wherein a mass ratio of the components (A) and (B) in total to the component (C), [((A)+(B))/(C)], is preferably 0.02 or more, more preferably 0.05 or more, further more preferably 0.1 or more, and particularly preferably 0.23 or more, and is preferably 3 or less, more preferably 0.8 or less, further more preferably 0.6 or less, and particularly preferably 0.3 or less.

<21> The external skin preparation according to any of <1> to <19>, wherein a mass ratio of the components (A) and (B) in total to the component (C), [((A)+(B))/(C)], is preferably 0.02 or more and 3 or less, more preferably 0.05 or more and 0.8 or less, further more preferably 0.1 or more and 0.6 or less, and particularly preferably 0.23 or more and 0.3 or less.

<22> The external skin preparation according to <13> or <14>, wherein a mass ratio of the component (C-2) to the component (C-1), [(C-2)/(C-1)], is preferably 0.5 or more, more preferably 1 or more, further more preferably 3 or more, and particularly preferably 6 or more, and is preferably 600 or less, more preferably 100 or less, further more preferably 25 or less, and particularly preferably 9 or less.

<23> The external skin preparation according to any of <1> to <22>, preferably further comprising one or more selected from the group consisting of (D) a non-volatile liquid oil (provided that the component (A) is excluded) and (E) a film forming agent, more preferably the components (A) to (D), and further more preferably the components (A) to (E).

<24> The external skin preparation according to <23>, wherein the component (D) is preferably one or more selected from the group consisting of a non-volatile ester oil, a non-volatile hydrocarbon oil, and a non-volatile silicone oil, more preferably a non-volatile ester oil, further more preferably one or more selected from the group consisting of a non-volatile fatty acid ester oil and a non-volatile aromatic carboxylic acid ester oil, further more preferably one or more selected from the group consisting of a non-volatile monohydric alcohol fatty acid ester oil, a non-volatile polyhydric alcohol fatty acid ester oil, and a non-volatile aromatic carboxylic acid ester oil, further more preferably one or more selected from the group consisting of a non-volatile monohydric alcohol fatty acid ester oil and a non-volatile aromatic carboxylic acid ester oil, and particularly preferably one or more selected from the group consisting of cetyl 2-ethylhexanoate, isononyl isononanoate, isotridecyl isononanoate, isopropyl myristate, isopropyl palmitate, 2-ethylhexyl palmitate, 2-ethylhexyl stearate, stearyl stearate, and C12-15 alkyl benzoate.

<25> The external skin preparation according to <23> or <24>, wherein a content of the component (D) is preferably 0.1% by mass or more, more preferably 0.5% by mass or more, and further more preferably 1% by mass or more based on the external skin preparation, and is preferably 35% by mass or less, more preferably 25% by mass or less, further more preferably 20% by mass or less, and particularly preferably 10% by mass or less based on the external skin preparation.

<26> The external skin preparation according to <23> or <24>, wherein a content of the component (D) is preferably 0.1% by mass or more and 35% by mass or less, more preferably 0.5% by mass or more and 25% by mass or less, further more preferably 1% by mass or more and 20% by mass or less, and particularly preferably 1% by mass or more and 10% by mass or less based on the external skin preparation.

<27> The external skin preparation according to any of <23> to <26>, wherein a mass ratio of the component (B) to the components (A) and (D) in total, [(B)/((A)+(D))], is preferably 0.01 or more, more preferably 0.05 or more, and further more preferably 0.1 or more, and is preferably 1 or less, more preferably 0.5 or less, further more preferably 0.25 or less, and particularly preferably 0.18 or less.

<28> The external skin preparation according to any of <23> to <26>, wherein a mass ratio of the component (B) to the components (A) and (D) in total, [(B)/((A)+(D))], is preferably 0.01 or more and 1 or less, more preferably 0.05 or more and 0.5 or less, further more preferably 0.1 or more and 0.25 or less, and particularly preferably 0.1 or more and 0.18 or less.

<29> The external skin preparation according to any of <23> to <28>, wherein the component (E) is preferably one or more selected from the group consisting of a silicone-based film forming agent and a (meth)acrylic film forming agent, more preferably a silicone-based film forming agent, further more preferably one or more selected from the group consisting of a poly(N-acylalkyleneimine) modified silicone, an amino modified silicone, fluorine modified silicone, trimethylsiloxysilicate, a trimethylsiloxysilicate/dimethiconol crosspolymer, a (meth)acrylic polymer having a dendrimer type siloxane structure in a side chain, polyalkylsilsesquioxane, and a (meth)acrylic silicone-based graft copolymer, further more preferably one or more selected from the group consisting of a poly(N-acylalkyleneimine) modified silicone and trimethylsiloxysilicate, and particularly preferably a poly(N-acylalkyleneimine) modified silicone, or a combination of a poly(N-acylalkyleneimine) modified silicone and trimethylsiloxysilicate.

<30> The external skin preparation according to <29>, wherein the poly(N-acylalkyleneimine) modified silicone is one or more selected from the group consisting of a poly(N-formyl ethyleneimine) modified silicone, a poly(N-acetylethyleneimine) modified silicone, a poly(N-propionylethyleneimine) modified silicone, a poly(N-n-octanoylethyleneimine) modified silicone, a poly(N-n-dodecanoylethyleneimine) modified silicone, a poly(N-formylpropylenimine) modified silicone, a poly(N-acetylpropyleneimine) modified silicone, a poly(N-propionylpropyleneimine) modified silicone, a poly(N-n-octanoylpropyleneimine) modified silicone, and a poly(N-n-dodecanoylpropyleneimine) modified silicone.

<31> The external skin preparation according to any of <23> to <30>, wherein a content of the component (E) is preferably 0.1% by mass or more, more preferably 0.5% by mass or more, further more preferably 0.75% by mass or more, and particularly preferably 1% by mass or more based on the external skin preparation, and is preferably 10% by mass or less, more preferably 7.5% by mass or less, further more preferably 5% by mass or less, and particularly preferably 4° by mass or less based on the external skin preparation.

<32> The external skin preparation according to any of <23> to <30>, wherein a content of the component (E) is preferably 0.1% by mass or more and 10% by mass or less, more preferably 0.5% by mass or more and 7.5% by mass or less, further more preferably 0.75% by mass or more and 5% by mass or less, and particularly preferably 1% by mass or more and 4% by mass or less based on the external skin preparation.

<33> The external skin preparation according to any of <1> to <32>, wherein a content of a ultraviolet scattering agent is preferably 0% by mass or more and 2.5% by mass or less, more preferably 0% by mass or more and 1° by mass or less, further more preferably 0° by mass or more and 0.5° by mass or less, and particularly preferably 0% by mass based on the external skin preparation.

<34> The external skin preparation according to any of <1> to <33>, wherein a content of a surfactant is preferably 0% by mass or more and 2.5% by mass or less, more preferably 0% by mass or more and 1% by mass or less, further more preferably 0% by mass or more and 0.5% by mass or less, and particularly preferably 0% by mass based on the external skin preparation.

<35> The external skin preparation according to any of <1> to <34>, wherein a content of water is preferably 0° by mass or more and 10° by mass or less, more preferably 0° by mass or more and 5° by mass or less, further more preferably 0% by mass or more and 0.5% by mass or less, and particularly preferably 0% by mass based on the external skin preparation.

<36> The external skin preparation according to any of <1> to <35>, wherein the external skin preparation is preferably a transparent liquid, an emulsion, a paste, a cream, a gel, a lotion, a spray, or a foam, more preferably a spray, further more preferably an aerosol spray type external skin preparation or a non-aerosol spray type external skin preparation, and particularly preferably an aerosol spray type external skin preparation.

<37> The external skin preparation according to any of <1> to <36>, wherein the external skin preparation (the stock liquid for an aerosol type external skin preparation) is preferably liquid.

<38> The external skin preparation according to any of <1> to <37>, wherein the viscosity of the external skin preparation (the stock liquid for an aerosol type external skin preparation) at 25° C. is preferably 0 mPa·s or more, more preferably 2.5 mPa·s or more, further more preferably 5 mPa·s or more, and particularly preferably 10 mPa·s or more, and is preferably 20000 mPa·s or less, more preferably 10000 mPa·s or less, further more preferably 2500 mPa·s or less, further more preferably 1500 mPa·s or less, and particularly preferably less than 500 mPa·s.

<39> An aerosol type external skin preparation, wherein a stock liquid comprising the following components (A), (B), and (C):
(A) an oil-soluble ultraviolet absorber;
(B) 0.5% by mass or more and 20% by mass or less of an oil gelling agent based on the stock liquid; and
(C) 50% by mass or more of a non-aqueous volatile component based on the stock liquid,
(optionally, in addition, the component (D) and/or the component (E), and other components) and a propellant are charged in a pressure proof container, provided that the stock liquid is the total composition of a content of liquid excluding the propellant.

<40> The external skin preparation according to <39>, wherein the external skin preparation is preferably an aerosol spray type or an aerosol foam type external skin preparation, and more preferably an aerosol spray type external skin preparation.

<41> The external skin preparation according to any of <1> to <40>, wherein the external skin preparation is preferably a sunscreen.

EXAMPLES

Hereinafter, the present invention will be described in detail with reference to Examples, but the present invention is not limited to these Examples.

Examples 1 to 15 and Comparative Examples 1 to 4 Aerosol Spray Type Oil-Based External Skin Preparation Aerosol spray type oil-based external skin preparations were manufactured, and the measurement and evaluation described below were performed. Table 1 to Table 3 show the results.

(Production Method)

In accordance with the formulations shown in Table 1 to Table 3, respective components were uniformly mixed using a homomixer provided with a paddle blade to prepare stock liquids of aerosol spray type oil-based external skin preparations. Each resulting stock liquids was charged in pressure proof containers for aerosol with a propellant (LPG) such that the pressure in the pressure proof container can be 0.22 MPa (25° C.) and the ratio of stock liquid:propellant=40:60 (mass ratio) can be satisfied.

For the evaluation of the impression from use, those charged in the pressure proof container for aerosol of the following specification 1 were used, and for the evaluation of being unlikely to drip, those charged in the pressure proof container for aerosol of the following specification 2 were used.

Specification 1 manufactured by precision valve Japan, stem: 04-5241, housing: 07-5166, button: 20-1213-0146

Specification 2 manufactured by Mitani Valve Co., Ltd., metering valve: C16-HCP4B22(51)314HG8101(ALPS2)34 (10), button: P94W 05112D"3"

(Measurement Method and Evaluation Method)

(1) Viscosity

Each stock liquid of the oil-based external skin preparation (before being charged into a pressure proof container) was charged in a glass bottle with a lid, and the viscosity at 25° C. on the next day of preparation was measured. For the measurement, a B-type viscometer (TVB-10) manufactured by TOKI SANGYO CO., LTD was used. After the inside of the glass bottle was previously stirred, the viscosity was measured under the conditions of rotor: No. 2, rotational speed: 60 rpm, measurement time: 1 minute, and evaluated under the following criteria. The viscosity of the stock liquid of the oil-based external skin preparation of Example 1 was 27 mPa·s, and the viscosity of the stock liquid of the oil-based external skin preparation of Example 2 was 29 mPa·s.

(Evaluation Criteria of Viscosity)
a: less than 500 mPa·s
b: 500 mPa·s or more (2) Viscosity after Volatilization of Volatile Components The components excluding volatile components (the component (C) for Examples 1 to 14 and Comparative Examples 1 to 4, and the component (C) and water for Example 15) (that is, corresponding to the components on the skin after the spray was sprayed onto the skin) were prepared from the composition of each stock liquid of the oil-based external skin preparation, each of them was charged in a glass bottle with a lid, and the viscosity at 25° C. on the next day of preparation was measured as the viscosity after volatilization of the volatile components. For the measurement, a B-type viscometer (TVB-10) manufactured by TOKI SANGYO CO., LTD was used. The viscosity was measured under the conditions of rotor: T-C, rotational speed: 5 rpm, measurement time: 1 minute, and evaluated under the following criteria. The viscosity after volatilization of volatile components of the oil-based external skin preparation of Example 1 was 400000 mPa·s, and the viscosity after volatilization of volatile components of the oil-based external skin preparation of Example 2 was 340000 mPa·s.

(Evaluation Criteria of Viscosity after Volatilization of Volatile Components)
a: 10000 mPa·s or more
b: less than 10000 mPa·s (3) SPF 1.3 g/cm' of each stock liquid of the oil-based external skin preparation before being charged into a pressure proof container was weighed on a HelioPlates HD6 (manufactured by Labsphere), spread by a finger covered with a fingertip for 30 seconds, and dried for 15 minutes, and then, the SPF value was measured using an SPF ANALYZER (UV-2000S, manufactured by Labsphere) and evaluated under the following criteria. The SPF value of the oil-based external skin preparation of Example 1 was 95.6, and the SPF value of the oil-based external skin preparation of Example 2 was 94.7.

(SPF Evaluation Criteria)
5: very high (SPF 90 or more)
4: relatively high (SPF 70 or more and less than 90)
3: slightly high (SPF 50 or more and less than 70)
2: acceptable limit (SPF 20 or more and less than 50)
1: low (less than SPF 20)

(4) Uniformity 0.03 g of each stock liquid of the oil-based external skin preparation before being charged into a pressure proof container was weighed on a PMMA plate, spread by a finger covered with a fingertip for 1 minute, and the application state was observed by a VISIA-CR (manufactured by Canfield Scientific). Blue components were extracted from the obtained image (RGB), and the mean reflection absorbance and the standard deviation were calculated from the images before and after application. This mean reflection absorbance was divided by the standard deviation, and the variation (CV value) was calculated. Uniformity was evaluated under the following criteria. FIG. 1 shows the photographed images of Example 7 and Comparative Example 1.

(Evaluation Criteria of Uniformity)
AAA: CV value less than 0.06
AA: CV value 0.06 or more and less than 0.07
A: CV value 0.07 or more and less than 0.1
B: CV value 0.1 or more (5) Absence of Strong Oiliness (Oily Feeling) and Tightness The impression from use (absence of strong oiliness and strong tightness) of each oil-based external skin preparation was subjected to sensory evaluation by 15 professional panelists under the following criteria. The average of the scores by 15 panelists was employed as the score of each oil-based external skin preparation (the score was rounded off to the first decimal place). An appropriate amount of the oil-based external skin preparation was sprayed onto the inner side of the forearm, and then conditioned with hand, followed by evaluation.

(Evaluation Criteria of Impression from Use)
Score 5: Unpleasant oiliness and unpleasant tightness are not felt.
Score 4: Unpleasant oiliness and unpleasant tightness are not so much felt.
Score 3: Unpleasant oiliness and unpleasant tightness are slightly felt.
Score 2: Unpleasant oiliness and unpleasant tightness are felt, but are within the acceptable limit.
Score 1: Unpleasant oiliness and unpleasant tightness are strongly felt.

(6) Unlikeliness to Drip

Each oil-based external skin preparation (to enable spraying of the same amount of the oil-based external skin preparation, a one-push valve (manufactured by Mitani Valve Co., Ltd.) was used) was placed on a table, a black plastic board was allowed to stand vertically on the table 6 cm apart from the injection port of the oil-based external skin preparation. Each oil-based external skin preparation was sprayed towards the surface of this black plastic board with one push, the surface of the black plastic board was visually observed for 10 seconds, and being unlikely to drip was evaluated under the following criteria.

(Evaluation Criteria of being Unlikely to Drip)
3: no dripping
2: gently dripped
1: vigorously dripped

TABLE 1

| | Component (% by mass) | Example | | | | | | |
| --- | --- | --- | --- | --- | --- | --- | --- | --- |
| | | 1 | 2 | 3 | 4 | 5 | 6 | 7 |
| A | 2-Ethylhexyl p-methoxycinnamate *1 | 10.0 | 10.0 | 10.0 | 3.0 | 10.0 | 10.0 | 10.0 |
| A | Diethylamino hydroxybenzoyl hexyl benzoate *2 | 2.5 | 2.5 | 10.0 | 1.0 | 2.5 | 2.5 | 2.5 |
| A | Bis-ethylhexyloxyphenol methoxyphenyl triazine *3 | 0.5 | 0.5 | 3.0 | 0.5 | 0.5 | 0.5 | 0.5 |
| A | Ethylhexyl triazone *4 | 3.0 | 3.0 | 3.0 | 0.5 | 3.0 | 3.0 | 3.0 |
| B | Dextrin palmitate *5 | 3.0 | 3.0 | 3.0 | 2.0 | 0.5 | 2.0 | 20.0 |
| B | Inulin stearate *11 | 0.0 | 0.0 | 0.0 | 0.0 | 0.0 | 0.0 | 0.0 |
| B | Dibutyl ethylhexanoyl glutamide *12 | 0.0 | 0.0 | 0.0 | 0.0 | 0.0 | 0.0 | 0.0 |
| C-1 | Dimethylpolysiloxane *6 | 6.0 | 6.0 | 0.1 | 0.1 | 6.0 | 6.0 | 6.0 |
| C-1 | Volatile dimethicone *13 | 2.0 | 2.0 | 0.0 | 0.0 | 2.0 | 2.0 | 2.0 |
| C-2 | Ethanol | 64.8 | 64.8 | 50.0 | 57.9 | 67.3 | 65.8 | 47.8 |
| C-3 | Isododecane | 0.0 | 0.0 | 0.0 | 0.0 | 0.0 | 0.0 | 0.0 |
| | Purified water | 0.0 | 0.0 | 0.0 | 0.0 | 0.0 | 0.0 | 0.0 |
| D | C12-15 Alkyl benzoate *7 | 0.0 | 5.0 | 20.0 | 34.0 | 0.0 | 0.0 | 0.0 |
| D | Isopropyl palmitate *8 | 5.0 | 0.0 | 0.9 | 1.0 | 5.0 | 5.0 | 5.0 |

TABLE 1-continued

|   | Component (% by mass) | Example 1 | Example 2 | Example 3 | Example 4 | Example 5 | Example 6 | Example 7 |
|---|---|---|---|---|---|---|---|---|
| E | Poly(N-propionylethyleneimine) modified silicone *9 | 1.2 | 1.2 | 0.0 | 0.0 | 1.2 | 1.2 | 1.2 |
| E | Trimethylsiloxysilicate *10 | 2.0 | 2.0 | 0.0 | 0.0 | 2.0 | 2.0 | 2.0 |
|   | Total | 100.0 | 100.0 | 100.0 | 100.0 | 100.0 | 100.0 | 100.0 |
|   | Component (C) content (% by mass) | 72.8 | 72.8 | 50.1 | 58.0 | 75.3 | 73.8 | 55.8 |
|   | Viscosity | a | a | a | a | a | b | b |
|   | Viscosity after volatilization of volatile components | a | a | a | a | a | b | b |
|   | Evaluation of SPF | 5 | 5 | 5 | 2 | 3 | 4 | 5 |
| Uniformity | CV value | 0.056 | 0.057 | 0.073 | 0.074 | 0.077 | 0.057 | 0.049 |
|   | Evaluation | AAA | AAA | A | A | A | AAA | AAA |
|   | Absence of strong oiliness and strong tightness | 4.9 | 4.9 | 4.8 | 4.7 | 5.0 | 5.0 | 1.7 |
|   | Difficulty in dripping | 3 | 3 | 3 | 3 | 2 | 2 | 3 |

TABLE 2

|   | Component (% by mass) | Ex. 8 | Ex. 9 | Ex. 10 | Ex. 11 | Ex. 12 | Ex. 13 | Ex. 14 | Ex. 15 |
|---|---|---|---|---|---|---|---|---|---|
| A | 2-Ethylhexyl p-methoxycinnamate *1 | 10.0 | 10.0 | 10.0 | 10.0 | 10.0 | 10.0 | 10.0 | 10.0 |
| A | Diethylamino hydroxybenzoyl hexyl benzoate *2 | 2.5 | 2.5 | 2.5 | 2.5 | 2.5 | 2.5 | 2.5 | 2.5 |
| A | Bis-ethylhexyloxyphenol methoxyphenyl triazine *3 | 0.5 | 0.5 | 0.5 | 0.5 | 0.5 | 0.5 | 0.5 | 0.5 |
| A | Ethylhexyl triazone *4 | 3.0 | 3.0 | 3.0 | 3.0 | 3.0 | 3.0 | 3.0 | 3.0 |
| B | Dextrin palmitate *5 | 0.0 | 0.0 | 3.0 | 3.0 | 3.0 | 3.0 | 3.0 | 3.0 |
| B | Inulin stearate *11 | 3.0 | 0.0 | 0.0 | 0.0 | 0.0 | 0.0 | 0.0 | 0.0 |
| B | Dibutyl ethylhexanoyl glutamide *12 | 0.0 | 3.0 | 0.0 | 0.0 | 0.0 | 0.0 | 0.0 | 0.0 |
| C-1 | Dimethylpolysiloxane *6 | 6.0 | 6.0 | 0.0 | 6.0 | 0.0 | 8.0 | 0.0 | 6.0 |
| C-1 | Volatile dimethicone *13 | 2.0 | 2.0 | 1.0 | 2.0 | 1.0 | 0.0 | 1.0 | 2.0 |
| C-2 | Ethanol | 64.8 | 64.8 | 72.8 | 69.8 | 77.8 | 68.0 | 64.8 | 58.8 |
| C-3 | Isododecane | 0.0 | 0.0 | 0.0 | 0.0 | 0.0 | 0.0 | 8.0 | 0.0 |
|   | Purified water | 0.0 | 0.0 | 0.0 | 0.0 | 0.0 | 0.0 | 0.0 | 6.0 |
| D | C12-15 Alkyl benzoate *7 | 0.0 | 0.0 | 0.0 | 0.0 | 0.0 | 0.0 | 0.0 | 5.0 |
| D | Isopropyl palmitate *8 | 5.0 | 5.0 | 5.0 | 0.0 | 0.0 | 5.0 | 5.0 | 0.0 |
| E | Poly(N-propionylethyleneimine) modified silicone *9 | 1.2 | 1.2 | 1.2 | 1.2 | 1.2 | 0.0 | 1.2 | 1.2 |
| E | Trimethylsiloxysilicate *10 | 2.0 | 2.0 | 1.0 | 2.0 | 1.0 | 0.0 | 1.0 | 2.0 |
|   | Total | 100.0 | 100.0 | 100.0 | 100.0 | 100.0 | 100.0 | 100.0 | 100.0 |
|   | Component (C) content (% by mass) | 72.8 | 72.8 | 73.8 | 77.8 | 78.8 | 76.0 | 73.8 | 66.8 |
|   | Viscosity | a | a | a | a | a | a | a | a |
|   | Viscosity after volatilization of volatile components | a | a | a | a | a | a | a | a |
|   | Evaluation of SPF | 5 | 3 | 5 | 5 | 5 | 4 | 3 | 5 |
| Uniformity | CV value | 0.068 | 0.072 | 0.060 | 0.066 | 0.070 | 0.061 | 0.058 | 0.062 |
|   | Evaluation | AA | A | AA | AA | A | AA | AAA | AA |
|   | Absence of strong oiliness and strong tightness | 4.8 | 4.8 | 4.7 | 5.0 | 4.5 | 4.4 | 4.1 | 4.7 |
|   | Difficulty in dripping | 3 | 3 | 3 | 3 | 3 | 3 | 3 | 3 |

TABLE 3

|   | Component (% by mass) | Comp. Ex. 1 | Comp. Ex. 2 | Comp. Ex. 3 | Comp. Ex. 4 |
|---|---|---|---|---|---|
| A | 2-Ethylhexyl p-methoxycinnamate *1 | 10.0 | 10.0 | 10.0 | 10.0 |
| A | Diethylamino hydroxybenzoyl hexyl benzoate *2 | 2.5 | 2.5 | 2.5 | 2.5 |
| A | Bis-ethylhexyloxyphenol methoxypheryl triazine *3 | 0.5 | 0.5 | 0.5 | 0.5 |
| A | Ethylhexyl triazone *4 | 3.0 | 3.0 | 3.0 | 3.0 |
| B | Dextrin palmitate *5 | 0.0 | 0.1 | 25.0 | 3.0 |
| B | Inulin stearate *11 | 0.0 | 0.0 | 0.0 | 0.0 |
| B | Dibutyl ethylhexanoyl glutamide *12 | 0.0 | 0.0 | 0.0 | 0.0 |
| C-1 | Dimethylpolysiloxane *6 | 6.0 | 6.0 | 6.0 | 6.0 |
| C-1 | Volatile dimethicone *13 | 2.0 | 2.0 | 2.0 | 2.0 |
| C-2 | Ethanol | 67.8 | 67.7 | 42.8 | 20.0 |
| C-3 | Isododecane | 0.0 | 0.0 | 0.0 | 0.0 |
|   | Purified water | 0.0 | 0.0 | 0.0 | 0.0 |
| D | C12-15 Alkyl benzoate *7 | 0.0 | 0.0 | 0.0 | 49.8 |
| D | Isopropyl palmitate *8 | 5.0 | 5.0 | 5.0 | 0.0 |
| E | Poly(N-propionylethyleneimine) modified silicone *9 | 1.2 | 1.2 | 1.2 | 1.2 |
| E | Trimethylsiloxysilicate *10 | 2.0 | 2.6 | 2.61 | 2.0 |
| Total |   | 100.0 | 100.0 | 100.6 | 100.0 |
| Component (C) content (% by mass) |   | 75.8 | 75.7 | 50.8 | 28.0 |

TABLE 3-continued

|  | Comparative Example | | | |
|---|---|---|---|---|
| Component (% by mass) | 1 | 2 | 3 | 4 |
| Viscosity | a | a | a | a |
| Viscosity after volatilization of volatile components | b | b | a | a |
| Evaluation of SPF | 2 | 2 | 5 | 2 |
| Uniformity   CV value | 0.110 | 0.120 | 0.068 | 0.060 |
|              Evaluation | B | B | AA | AA |
| Absence of strong oiliness and strong tightness | 4.9 | 4.9 | 1.0 | 2.5 |
| Difficulty in dripping | 1 | 1 | 3 | 1 |

The symbols in the Tables represent the followings.
*1: Uvinul MC-80 (manufactured by BASF)
*2: Uvinul A plus (manufactured by BASF)
*3: Tinosorb S (manufactured by BASF)
*4: Uvinul T-150 (manufactured by BASF)
*5: Rheopearl KL2 (manufactured by Chiba Flour Milling Co., Ltd.)
*6: KF-96L-2cs (manufactured by Shin-Etsu Chemical Co., Ltd.)
*7: FINSOLV TN (manufactured by Innospec Active Chemicals)
*8: EXCEPARL IPP (manufactured by Kao Corporation)
*9: Prepared according to the description in Synthetic Example 1 in JP-A-2008-143820 (the numerical value in Table means a content of active components with respect to the external skin preparation.)
*10: KF-7312 L (manufactured by Shin-Etsu Chemical Co., Ltd. (the numerical value in Table means a content of active components with respect to the external skin preparation.))
*11: Rheopearl ISL2 (manufactured by Chiba Flour Milling Co., Ltd.)
*12: Amino acid-based gelling agent EB-21 (manufactured by AJINOMOTO CO., INC.)
*13: KF-96L-1.5cs (manufactured by Shin-Etsu Chemical Co., Ltd.)

The invention claimed is:

1. A non-aerosol spray external skin preparation comprising the following components (A), (B), and (C):
   (A) one or more of an ultraviolet absorber selected from the group consisting of 2-ethylhexyl p-methoxycinnamate, diethylamino hydroxybenzoyl hexyl benzoate, bis-ethylhexyloxyphenol methoxyphenyl triazine, and ethylhexyl triazone;
   (B) 0.5% by mass or more and 20% by mass or less of one or more of an oil gelling agent selected from the group consisting of dextrin palmitate, inulin stearate, and dibutylethylhexanol glutamide;
   (C) 50% by mass or more of a non-aqueous volatile component, comprising
      (C-1) dimethylpolysiloxane, and
      at least 40% by mass or more and 95% by mass or less of (C-2) ethanol, the mass % of (C-2) based on a total mass of component (C), wherein
   the % by mass of component (B) and component (C) are each based on total mass of the non-aerosol spray external skin preparation,
   the non-aerosol spray external skin preparation has a ratio of component (B) to component (A) of 0.031 to 0.6 by mass, and
   the non-aerosol spray external skin preparation comprises (D) a non-volatile liquid oil and (E) a film forming agent.

2. The external skin preparation according to claim 1, wherein the component (B) is dibutyl ethylhexanoyl glutamide.

3. The external skin preparation according to claim 1, wherein the component (B) is dextrin palmitate.

4. The external skin preparation according to claim 1, wherein a content of the component (B) is 0.5% by mass or more and 15% by mass or less, based on the total mass of the non-aerosol spray external skin preparation.

5. The external skin preparation according to claim 1, wherein a content of the component (B) is 2.5% by mass or more and 5% by mass or less, based on the total mass of the non-aerosol spray external skin preparation.

6. The external skin preparation according to claim 1, wherein the non-aerosol spray external skin preparation has a ratio of component (B) to component (A) of 0.1 to 0.6 by mass.

7. The external skin preparation according to claim 1, wherein the non-aerosol spray external skin preparation has a ratio of component (A) to component (C) of 0.01 to 1.5 by mass.

8. The external skin preparation according to claim 1, wherein the non-aerosol spray external skin preparation has a ratio of component (A) to component (C) of 0.15 to 0.5 by mass.

9. The external skin preparation according to claim 1, wherein the non-aerosol spray external skin preparation has a ratio of a total of components (A) and (B) to component (C) of 0.02 to 3 by mass.

10. The external skin preparation according to claim 1, wherein the non-aerosol spray external skin preparation has a ratio of a total of components (A) and (B) to component (C) of 0.1 to 0.6 by mass.

11. The external skin preparation according to claim 1, wherein the component (B) is inulin stearate.

12. The external skin preparation according to claim 1, wherein a content of the component (C) is 60% by mass or more and 80% by mass or less, based on the total mass of the non-aerosol spray external skin preparation.

13. The external skin preparation according to claim 1, wherein a content of (C-2) ethanol is 50% by mass or more and 80% by mass or less, the mass % of (C-2) based on the total mass of component (C).

14. The external skin preparation according to claim 1, wherein the component (A) comprises at least two selected from the group consisting of 2-ethylhexyl p-methoxycinnamate, diethylamino hydroxybenzoyl hexyl benzoate, bis-ethylhexyloxyphenol methoxyphenyl triazine, and ethylhexyl triazone.

15. The external skin preparation according to claim 1, wherein the component (A) comprises at least three selected from the group consisting of 2-ethylhexyl p-methoxycinnamate, diethylamino hydroxybenzoyl hexyl benzoate, bis-ethylhexyloxyphenol methoxyphenyl triazine, and ethylhexyl triazone.

16. The external skin preparation according to claim 1, wherein the component (A) comprises 2-ethylhexyl p-methoxycinnamate, diethylamino hydroxybenzoyl hexyl benzoate, bis-ethylhexyloxyphenol methoxyphenyl triazine, and ethylhexyl triazone.

17. The external skin preparation according to claim 1, wherein the component (A) comprises
   at least one selected from the group consisting of 2-ethylhexyl p-methoxycinnamate and diethylamino hydroxybenzoyl hexyl benzoate; and
   at least one selected from the group consisting of bis-ethylhexyloxyphenol methoxyphenyl triazine and ethylhexyl triazone.

18. The external skin preparation according to claim 1, wherein the component (D) is present in an amount of 1% by mass to 10% by mass, based on the total mass of the non-aerosol external skin preparation.

19. The external skin preparation according to claim 1, wherein the component (E) is present in an amount of 0.5% by mass to 7.5% by mass, based on the total mass of the non-aerosol external skin preparation.

20. The external skin preparation according to claim 1, wherein a content of the component (A) is 5% by mass or more and 30% by mass or less, based on the total mass of non-aerosol spray external skin preparation.

* * * * *